United States Patent [19]

Scher

[11] 4,440,563
[45] Apr. 3, 1984

[54] THIOLCARBAMATE SULFOXIDES STABILIZED WITH BUTYROLACTONE AND WATER

[75] Inventor: Herbert B. Scher, Moraga, Calif.

[73] Assignee: Stauffer Chemical Company, Westport, Conn.

[21] Appl. No.: 190,155

[22] Filed: Sep. 24, 1980

[51] Int. Cl.³ .......................................... A01N 43/00
[52] U.S. Cl. ......................................... 71/88; 71/94; 71/103
[58] Field of Search ...................... 71/103, 88, 94, 95; 260/343.6; 564/4

[56] References Cited

U.S. PATENT DOCUMENTS

| | | | |
|---|---|---|---|
| 2,898,373 | 8/1959 | Klaui | 260/343.6 |
| 3,005,830 | 10/1961 | Hort et al. | 260/343.6 |
| 3,119,877 | 1/1964 | Campbell et al. | 71/103 |
| 3,975,180 | 8/1976 | Gozzo et al. | 71/88 |
| 4,081,468 | 3/1978 | Baker et al. | 564/4 |
| 4,117,010 | 9/1978 | Baker et al. | 564/4 |

FOREIGN PATENT DOCUMENTS 2201331  7/1972  Fed. Rep. of Germany ... 260/343.6
47-22220  6/1972  Japan ................................. 260/343.6

OTHER PUBLICATIONS

Naito et al., "Stabilized Persulfate Soln. etc.," (1972), CA 77, No. 106802t (1972).
Mori et al., "Lactone Derivatives," (1977), CA 88, No. 6337d (1978).
Hessel, "Synergistic Nematocidal, etc.;" (1961), CA 55, p. 21466f, (1961).
Phrix-Werke, "Stabilizing Polyackylonitrile, etc.;" (1963), CA 61, p. 16257h, (1964).
Starks, "Stabilization of Chlorinated, etc.;" (1960), CA 55, p. 3878f, (1961).

*Primary Examiner*—Glennon H. Hollrah
*Attorney, Agent, or Firm*—Edwin H. Baker

[57] ABSTRACT

Herbicidal thiolcarbamate sulfoxide compositions of improved thermal stability.

10 Claims, No Drawings

THIOLCARBAMATE SULFOXIDES STABILIZED WITH BUTYROLACTONE AND WATER

BACKGROUND OF THE INVENTION

This invention relates to stabilized thiolcarbamate sulfoxide compositions.

DISCUSSION OF PRIOR ART

Thiolcarbamate sulfoxides of the type stabilized in accordance with the present invention are disclosed in U.S. Pat. Nos. 3,928,436, 3,879,455 and 3,989,684. While these compounds exhibit excellent herbicidal activity, they have been found to be somewhat thermally unstable. A study on the thermal stability of these compounds is reported in *The Journal of Chemistry and Industry*, Mar. 1, 1975, "On the thermal and Chemical Stability of Carbamoyl Sulfoxides," by Gozzo, Masoero, Santi, Galluzzi and Barton. U.S. Pat. No. 3,975,180 describes solid crystalline carbamyl sulfoxide/urea adducts which have improved thermal stability compared to the corresponding sulfoxide. Other patents teaching stabilized herbicidal sulfoxides are U.S. Pat. Nos. 4,081,468 and 4,117,010.

SUMMARY OF THE INVENTION

It has now been found that the thermal stability of certain thiolcarbamate sulfoxides can be improved by combining the sulfoxide with given amounts of butyrolactone and water. Accordingly, this invention relates to a novel composition of matter comprising:

(a) about 1 to 30 percent by weight of a thiolcarbamate sulfoxide of the formula

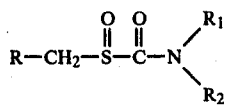

wherein

R is alkyl $C_1$–$C_7$, preferably $C_1$–$C_3$; haloalkyl $C_1$–$C_5$, preferably chloroalkyl $C_1$–$C_3$; alkoxy $C_1$–$C_5$, preferably $C_1$–$C_3$; and phenyl, most preferably R is alkyl $C_1$–$C_7$;

$R^1$ and $R^2$ independently are alkyl $C_1$–$C_6$; cycloalkyl $C_3$–$C_8$, preferably cyclohexyl; alkenyl $C_2$–$C_6$; and alkynyl $C_2$–$C_4$; and $R^1$ and $R^2$ together with the nitrogen atom to which they are attached form piperidino, hexamethyleneimino, decahydroquinolyl, 2,5-dimethylpiperidino and 5-ethyl-2-methylpiperidino; and correspondingly (b) about 99 to about 70 percent by weight of a mixture of water and butyrolactone, in a ratio of about 0.10 to about 3.0 parts by weight water per 1.0 part by weight butyrolactone.

Preferably, the novel composition of matter comprises (a) about 20 to about 30 percent by weight thiolcarbamate sulfoxide and (b) about 80 to about 70 percent by weight of the mixture of water and butyrolactone.

The preferred ratio of water to butyrolactone in said mixture is about 0.40 to about 1.0 part by weight water per 1.0 part by weight butyrolactone.

In addition to the above described stabilizing effect of the mixture of water and butyrolactone, other beneficial effects of the admixture with the thiolcarbamate sulfoxides have been observed. Firstly, it has been found that the thiolcarbamate sulfoxide is soluble in the mixture and the resulting solution is miscible with water. This phenomenon has the valuable benefit that the solution can be dispersed in water without the use of emulsifying or stabilizing agents and used in herbicidal applications directly.

Secondly, it has been found that the admixture of the thiolcarbamate sulfoxide and the butyrolactone and water has an unexpectedly low freezing point. This has the benefit that the mixture remains a liquid for low temperature herbicide applications.

Finally, it has been found that the water and butyrolactone have no adverse effect on the herbicidal activity of the thiolcarbamate sulfoxide, that is, the mixture of the thiolcarbamate sulfoxide, water and butyrolactone is herbicidally as active as the thiolcarbmate sulfoxide alone.

DETAILED DESCRIPTION OF THE INVENTION

The herbicidal thiolcarbmate sulfoxides stabilized in accordance with this invention are described in several publications, including, U.S. Pat. Nos. 3,897,492, 3,928,436, 3,879,455 and 3,989,684. Some examples of compounds of this type are: S-ethyl N,N-di-n-propyl carbamyl sulfoxide, S-ethyl N,N-di-i-butyl carbamyl sulfoxide, S-n-butyl N,N-di-isobutyl carbamyl sulfoxide, S-n-butyl N,N-di-isobutyl carbamyl sulfoxide, S-n-propyl N-n-butyl-Nethyl carbamyl sulfoxide, S-ethyl N-cyclohexyl-N-ethyl carbamyl sulfoxide, S-ethyl N-methyl-N-methylpropargyl carbamyl sulfoxide, S-n-propyl N,N-di-n-propyl carbamayl sulfoxide, S-ethyl N-allyl-N-npropyl carbamyl sulfoxide, S-n-chloropropyl N,N-diethyl carbamyl sulfoxide, S-ethoxyethenyl N,N-di-n-propyl carbamyl sulfoxide, S-isobutyl N-methyl-N-cyclohexylmethylcarbamyl sulfoxide, S-ethyl-hexahydro-1Hazepine-1-carbonyl sulfoxide, S-1,2-dichloropropyl N,N-di-i-propyl and the like.

The term "alkyl" as used herein refers to straight- or branched-chain saturated aliphatic hydrocarbon groups, i.e., methyl, ethyl, propyl, i-propyl, n-butyl, s-butyl and t-butyl.

The term "alkoxy" as used herein refers to a straight- or branched-chain saturated aliphatic hydrocarbonoxy group, i.e., methoxy, ethoxy, propoxy, i-propoxy, n-butoxy, i-butoxy, s-butoxy, and t-butoxy.

The term "halo" as used herein refers to chloro, bromo, and iodo.

The following example illustrates the stabilizing effect of the combination of water and butyrolactone as a stabilizer for a representative thiolcarbamate sulfoxide.

EXAMPLE I

2–3 Milliliters (ml) technical grade S-n-propyl N,N-di-n-propyl carbamyl sulfoxide (VS-I) were added to a 5 cc glass ampoule. The ampoule was sealed and placed in a constant temperature oven at 40° C. for one month. The same thiolcarbamate sulfoxide was dissolved in various amounts of water, butyrolactone (BLO) or mixtures of water and BLO and added to other 5 cc glass ampoules. These ampoules were sealed and were aged with the thiolcarbamate sulfoxide control sample.

At the end of the one month aging period, the samples were subjected to the analytical analysis to ascertain any thermal decomposition of the water-butyrolactone-thiolcarbamate sulfoxide combination versus the thiolcarbamate sulfoxide compound.

Analysis was run with a Hewlett Packard Model 1084 high pressure liquid chromatograph equipped with a microparticulate silica column and ultraviolet light detector operated at a wave length of 254 mu. The mobile phase for the analysis was a solvent mixture containing hexane, dichloromethane and methanol in volumentric ratios of 25:5:1, respectively. Test samples were prepared for analysis by mixing one milligram (mg) thiolcarbamate sulfoxide per ml of the mobile phase and shaking the mixture to ensure thorough mixing.

To calibrate the instrument, at least three injections of a calibration solution were made and UV response noted. The calibration solution was prepared by dissolving one mg of thiolcarbamate sulfoxide of known purity per ml of mobile phase. Purity of this standard thiolcarbamate sulfoxide was maintained by storage at 0° C.

A test sample solution was then injected into the chromatograph and UV response noted. If large numbers of samples were run, the instrument was periodically recalibrated. The amount of thiolcarbamate sulfoxide in a test sample was found by directly comparing the instrument UV respone for the test sample solution versus the response of the calibration solution. The co-efficient of variation was ascertained to be approximately two percent.

Table I shows the relative percent decomposition of S-n-propyl N,N-di-n-propyl carbamyl sulfoxide (VS-1) in combination with BLO and a mixture of water and BLO versus a sample of the thiolcarbamate sulfoxide (VS-1) alone.

TABLE I

STABILITY TEST

| Sample | Weight Percent | | | Relative Percent Decomposition at 40° C. for one month* |
|---|---|---|---|---|
| | VS-1 | Water | BLO | |
| 1 | 100 | none | none | 8.8 |
| 2 | 25 | none | 75 | 8.9 |
| 3 | 25 | 10 | 65 | 3.0 |

*First Order Decomposition

EXAMPLE II

The procedure of Example I was repeated except that a different batch of technical grade S-n-propyl N,N-di-n-propyl carbamyl sulfoxide (VS-2) was used in place of VS-1.

Table II shows the relative percent decomposition of VS-2 in combination with water and four different mixtures of water and BLO versus a sample of the thiolcarbamate sulfoxide (VS-2) alone.

TABLE II

STABILITY TEST

| Sample | Weight Percent | | | Relative Percent Decomposition at 40° C. for One month* |
|---|---|---|---|---|
| | VS-2 | Water | BLO | |
| 4 | 100 | none | none | 12.2 |
| 5 | 25 | 10 | 65 | 6.8 |
| 6 | 25 | 20 | 55 | 2.6 |
| 7 | 25 | 30 | 45 | 2.2 |
| 8 | 25 | 75 | none | 90.0 |

*First Order Decomposition

The liquid compositions of the present invention can be directly used as a herbicide without formulation with other ingredients. Preferably, the composition is diluted with water and applied as a herbicide in that form.

A surfactant can be included with the composition if desired. Such agents will usually comprise up to about 5 weight percent of the total composition.

The liquid compositions of the present invention are useful in controlling the growth of undesirable vegetation by pre-emergence or post-emergence application to the locus where control is desired, including pre-plant and post-plant soil incorporation as well as surface application.

In general, any conventional method of application can be used. The locus of application can be soil, seeds, seedlings, or the actual plants, as well as flooded fields. Soil application is preferred and can be achieved by conventional ground or air application equipment. In typical application, the compositions are applied to the soil surface.

The amount of the present composition which constitutes a herbicidally effective amount depends upon the nature of the plants to be controlled. The rate of application of active ingredients varies from about 0.01 to about 50 pounds per acre, preferably about 0.1 to about 25 pounds per acre with the actual amount used depending on the overall cost and the desired results.

What is claimed is:

1. A liquid herbicidal composition comprising a combination of
   (a) about 1 to about 30 percent by weight of a thiolcarbamate sulfoxide of the formula

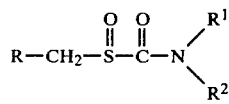

in which

R is alkyl $C_1$–$C_7$, haloalkyl $C_1$–$C_5$, alkoxy $C_1$–$C_5$ and phenyl;

$R^1$ and $R^2$ independently are alkyl $C_1$–$C_6$, cycloalkyl $C_3$–$C_8$, alkenyl $C_2$–$C_6$ and alkynyl $C_2$–$C_4$; or $R^1$ and $R^2$ together with the nitrogen atom to which they are attached form piperidino, hexamethyleneimino, decahydroquinolyl, 2,5-dimethylpiperidino and 5-ethyl-2-methylpiperidino; and (b) about 99 to about 70 percent by weight of a mixture of water and butyrolactone, in a ratio of about 0.10 to about 3.0 parts by weight water per 1.0 part by weight butyrolactone.

2. The composition according to claim 1 wherein the thiolcarbamate sulfoxide is present in an amount between about 20% by weight to about 30% by weight and the mixture is present in an amount between about 80% by weight to about 70% by weight.

3. The composition according to claim 1 wherein the thiolcarbamate sulfoxide is S-n-propyl N,N-di-n-propyl carbamyl sulfoxide.

4. The composition according to claim 2 wherein the thiolcarbamate sulfoxide is S-n-propyl N,N-di-n-propyl carbamyl sulfoxide.

5. The composition according to claim 1 wherein the ratio of water to butyrolactone in the mixture is about 0.40 to about 1.0 parts by weight water per 1.0 part by weight butyrolactone.

6. The composition according to claim 2 wherein the ratio of water to butyrolactone in the mixture is about 0.40 to about 1.0 parts by weight water per 1.0 part by weight butyrolactone.

7. The composition according to claim 4 wherein the ratio of water to butyrolactone in the mixture is about 0.40 to about 1.0 parts by weight water per 1.0 part by weight butyrolactone.

8. The composition according to claim 1 wherein R is alkyl $C_1$–$C_7$, $R^1$ and $R^2$ independently are alkyl $C_1$–$C_6$, cycloalkyl $C_3$–$C_8$ or $R^1$ and $R^2$ taken together with the nitrogen atom to which they are attached form piperidino, hexamethyleneimino, decahydroquinolyl, 2,5-dimethylpiperidino and 5-ethyl-2-methylpiperidino.

9. The composition according to claim 2 wherein the thiolcarbamate sulfoxide is S-n-propyl N,N-di-n-propyl carbamoyl sulfoxide and the ratio of water to butyrolactone in the mixture is about 0.40 to about 1.0 parts by weight water per 1.0 parts by weight butyrolactone.

10. The composition according to claim 1 wherein R is alkyl $C_1$–$C_3$, $R^1$ and $R^2$ independently are alkyl $C_1$–$C_6$.

* * * * *